(12) United States Patent
Akura et al.

(10) Patent No.: US 10,130,350 B2
(45) Date of Patent: Nov. 20, 2018

(54) PUPIL EXPANDER

(71) Applicant: Junsuke Akura, Wakayama (JP)

(72) Inventors: Junsuke Akura, Wakayama (JP); Kiran Pkharel, Hyogo (JP)

(73) Assignee: Junsuke Akura, Wakayama (JP)

( * ) Notice: Subject to any disclaimer, the term of this patent is extended or adjusted under 35 U.S.C. 154(b) by 345 days.

(21) Appl. No.: 14/780,676

(22) PCT Filed: Mar. 10, 2014

(86) PCT No.: PCT/JP2014/056140
§ 371 (c)(1),
(2) Date: Sep. 28, 2015

(87) PCT Pub. No.: WO2014/156583
PCT Pub. Date: Oct. 2, 2014

(65) Prior Publication Data
US 2016/0051244 A1 Feb. 25, 2016

(30) Foreign Application Priority Data
Mar. 29, 2013 (JP) ................................. 2013-071191

(51) Int. Cl.
A61B 17/02 (2006.01)
A61F 9/007 (2006.01)
A61B 17/00 (2006.01)
(52) U.S. Cl.
CPC ...... *A61B 17/0231* (2013.01); *A61B 17/0206* (2013.01); *A61B 17/0293* (2013.01); *A61B 2017/00862* (2013.01); *A61F 9/00736* (2013.01)

(58) Field of Classification Search
CPC ..... A61B 17/02; A61B 17/0231; A61F 9/007; A61F 9/0026; A61F 2/1662; A61F 2009/0052
See application file for complete search history.

(56) References Cited

U.S. PATENT DOCUMENTS 4,387,706 A 6/1983 Glass
5,163,419 A 11/1992 Goldman
(Continued)

FOREIGN PATENT DOCUMENTS

JP 7-194643 A 8/1995
JP 9-505753 A 6/1997
(Continued)

OTHER PUBLICATIONS

International Search Report dated Apr. 8, 2014 issued in corresponding PCT/JP2014/056140 application (pp. 1-3).

*Primary Examiner* — Anu Ramana
(74) *Attorney, Agent, or Firm* — Millen, White, Zelano & Branigan, P.C.; William Nixon

(57) ABSTRACT

The pupil expander 1 of the present invention is used to maintain a pupil in an expanded state during ophthalmologic surgery such as, e.g., cataract surgery. The pupil expander 1 is equipped with four arm sections 10 arranged serially in a manner as to form a circular shape as a whole and joint sections 20 which connect end sections of adjacent arm sections in a movable manner. With this, since the end sections of adjacent arm sections 10 are connected in a movable manner and therefore the entire shape of the pupil expander 1 can be deformed in an eye via the joint section 20, the pupil expander can be arranged safely without damaging an iris I, which enables easy and assured maintenance of a sufficiently expanded state of a pupil.

10 Claims, 9 Drawing Sheets

(56) References Cited

U.S. PATENT DOCUMENTS

| | | | |
|---|---|---|---|
| 5,354,331 A | 10/1994 | Schachar | |
| 5,374,272 A | 12/1994 | Apra et al. | |
| 5,427,088 A | 6/1995 | Graether | |
| 5,441,045 A | 8/1995 | Federman et al. | |
| 6,068,643 A | 5/2000 | Milverton | |
| 6,497,724 B1 * | 12/2002 | Stevens | A61F 2/07 623/1.15 |
| 8,900,136 B2 * | 12/2014 | Cote | A61F 9/00736 600/208 |
| 2008/0269888 A1 | 10/2008 | Malyugin | |
| 2012/0059404 A1 | 3/2012 | Eakins et al. | |

FOREIGN PATENT DOCUMENTS

| | | |
|---|---|---|
| JP | 2002-531170 A | 9/2002 |
| JP | 3688722 B2 | 8/2005 |
| JP | 2010-521229 A | 6/2010 |
| WO | 1993/14703 A1 | 8/1993 |
| WO | 1995/015120 A1 | 6/1995 |
| WO | 1999017684 A1 | 4/1999 |
| WO | 2008115455 A1 | 9/2008 |

* cited by examiner

PUPIL EXPANDER

FIELD OF THE INVENTION

The present invention relates to a pupil expander to be used to maintain an expanded state of a pupil during ophthalmologic surgery such as, e.g., cataract surgery.

DISCUSSION OF THE RELATED ART

Normally, a human eye has a function of adjusting an amount of light entering through a pupil positioned in the center of the iris. An iris is a ring-shaped tela positioned behind a cornea and forward of a crystalline lens, and has a central opening forming a pupil. An iris is structured by stretchable rough connective tissues and muscles for expanding and contracting a pupil. In a bright place, the tela of the iris expands centripetally to reduce the pupil (contract the pupil) so that the amount of light entering into the eye is reduced. In a dark place, the tela of the iris shrinks toward its root (peripheral portion of the pupil) to enlarge the pupil (expand the pupil) so that the amount of light entering into the eye is increased.

In the meantime, as one of diseases occurring in a human eye, there is a disorder called cataract which causes clouding of the crystalline lens with aging, resulting in reduced visual acuity. In a current cataract surgery, it is a mainstream to apply ultrasound crystalline lens emulsification suction surgery and intraocular lens insertion surgery. In this surgery, a circular incision of about 5 to 6 mm is formed in the center of the anterior capsule of the lens capsule. Then, the contents of the opacified crystalline lens is removed by suction via the incision, and an intraocular lens is inserted into the lens capsule through the incision.

In order to complete surgery of a crystalline lens, a vitreous body, or a retina inside an eye ball positioned behind an iris, such as, e.g., cataract surgery or vitreoretinal surgery, it is required to maintain the pupil in a sufficiently expanded (mydriasis) state (about 5 to 6 mm) during the surgery. However, in the case of an eye in which inflammation was present in the iris in the past, an eye in which eye drops of miotic agent were used for a long period of time for glaucoma, an eye in which pseudoexfoliation materials are adhered to an iris, or an eye in which senile pupillary constriction is strong, there is a case in which the pupil cannot be brought into a sufficiently expanded state even if a mydriatic agent is used before the surgery.

For an eye that the pupil cannot be brought into a fully expanded state as mentioned above, an iris retractor having a tip end section formed into a hook shape has been conventionally used (see, for example, the following Patent Document 1). The following explanation will be made by exemplifying a case using four iris retractors. When arranging these iris retractors, incisions are formed at four portions of the cornea and retractors are inserted into respective incisions. Then, the tip end sections of iris retractors are hooked to portions of the pupillary edges to pull the pupillary edges of the iris radially outward. In this state, using a silicon stopper, each of the iris retractor is fixed to the cornea to thereby maintain the state in which the diameter of the pupil is expanded to a sufficient size. Further, when removing the iris retractors, after loosening the fixing of the silicon stopper, the iris retractors are removed respectively. Such installations and removals of the iris retractors should be carefully performed so as not to damage the iris, which requires considerable effort and time. Especially, since the hooking portion for hooking the pupillary edge is made by a thin resin wire, there has been a problem that the pupillary edge of the iris is torn off when the pupillary edge of the iris is pulled by the iris retractor, resulting in deformation of the pupil after the surgery.

On the other hand, in recent years, as a device for expanding a pupil more simply and in a shorter time than the iris retractors mentioned above, a pupil expander, such as, e.g., Malyugin Ring, The OASIS Iris Expander, Morcher Pupil Dilator, is known (see, for example, the following Patent Documents 2 to 4). These pupil expanders are constituted by plastic high in shape memory property, and formed into a square shape in a natural state, or an approximately ring-shape with one opened section. The pupil expander of this kind is stored in a dedicated injector in an elongate folded manner, and introduced into an eye through a small incision of about 2.2 to 3.2 mm to be fitted to the pupillary edge of the iris. The pupil expander expands the pupil radially outward with the pupillary edge of the iris hooked by iris engaging portions, which are formed at 4 to 5 portions or formed along approximately the entire circumference, from the inner side.

PRIOR ART DOCUMENT

Patent Document

[Patent Document 1] Japanese Unexamined Laid-open Application Publication No. H7-194643
[Patent Document 2] Japanese Translation of PCT International Application Publication No. 2010-521229
[Patent Document 3] Japanese Translation of PCT International Application Publication No. 2002-531170
[Patent Document 4] Japanese Translation of PCT International Application Publication No. H9-505753

SUMMARY OF THE INVENTION

Problems to be Solved by the Invention

However, the conventional pupil expander is made of a material high in shape memory property. Therefore, when released in an eye from the injector, the pupil expander returns to its original inherent shape (the shape in the natural state) inside the eye. Therefore, it expands into a square shape or a circular shape having a diameter of about 5 to 7 mm on the iris in the eye. For this reason, after hooking the iris engaging portion of the pupil expander with the pupillary edge using a medical device such as, e.g., a Sinskey hook, when hooking the adjacent or opposite side pupillary edge with another iris engaging portion, it is required to eccentrically move the iris engaging portion with the pupil wide opened. In view of this, since the difficulty of the work is not fully resolved, when arranging the pupil expander, there was a possibility that the iris tissue is damaged by the contact to the corneal endothelium important for maintaining the transparency of the cornea or the excessive stretching of the iris tissue.

Further, these pupil expanders can be placed in an eye in a moderate degree pupil expanded state. However, it is very difficult to place it to a pupil poor in the pupil expanded state or small in size, and therefore the pupil must be eccentrically expanded largely, which easily causes damages to the iris tissue.

Furthermore, in a conventional pupil expander, such as a Malyugin Ring, in order to compensate for the disadvantage that the expander returns to its original shape when inserted into an eye, the pupil expander is hooked to the pupillary edge while releasing the expander little by little in a state in which the injector is inserted in the eye. However, hooking the pupil expander to the pupillary edge of the iris is not easy itself, and therefore it is not easy for everyone to perform this operation. It becomes a very difficult task especially in cases where the pupil diameter is less than 3 mm. As for the removal, although the Malyugin Ring, etc., can be accommodated into the injector within the eye, there is a possibility that the iris may be damaged by the work.

The present invention was made in view of the aforementioned problems, and aims to provide a pupil expander capable of being arranged safely without damaging an iris during ophthalmologic surgery such as, e.g., cataract surgery, and also capable of maintaining a sufficiently expanded state of a pupil.

Means for Solving the Problems

In order to attain the aforementioned object, the present invention is characterized in that a pupil expander to be used to maintain an expanded state of a pupil during ophthalmologic surgery such as cataract surgery, includes four or more arm sections serially arranged in a manner as to form a circular shape, and joint sections configured to connect end sections of the arm sections arranged adjacently in a movable manner.

With this, since the end sections of adjacent arm sections are connected via the joint section in a movable manner and therefore the entire shape of the pupil expander can be deformed in an eye via each joint section, the pupil expander can be arranged safely without damaging the iris, which enables to maintain a sufficiently expanded state of the pupil.

Further, it is preferable that the joint section includes a first joint engagement section provided at one end section of the arm section on one side in a circumferential direction, and a second joint engagement section provided at the other end section of the arm section on the other side in the circumferential direction, and the first joint engagement section and the second joint engagement section are rotatable with each other. With this, the end sections of arm sections arranged adjacently via the first joint engagement section and the second joint engagement section can be connected easily and assuredly in a movable manner.

Further, it is preferable that the joint section rotatably supports the first joint engagement section and the second joint engagement section via a common rotation shaft. With this, the first joint engagement section and the second joint engagement section rotate in plain surfaces parallel with each other via a rotation shaft, and therefore the entire shape of the pupil expander can be deformed in the plane direction.

Further, it is preferable that the joint section is provided with a support section which rotatably supports the first joint engagement section and the second joint engagement section in a manner as to face the first joint engagement section and the second joint engagement section in a circumference direction. With this, the first joint engagement section and the second joint engagement section rotate in plain surfaces parallel with each other via a support section, and therefore the entire shape of the pupil expander can be deformed in the plane direction.

Further, it is preferable that the joint section has a predetermined frictional force for controlling rotational movements of the first joint engagement section and the second joint engagement section. With this, the rotational movements of the first joint engagement section and the second joint engagement section are controlled by the predetermined frictional force, which controls the movability of each of the arm sections provided with the first joint engagement section and the second joint engagement section. Therefore, even if the pupil expander receives an external force from the intraocular tissue such as, e.g., an iris, the entire shape of the pupil expander can be maintained assuredly.

Further, it is preferable that the joint section is provided with an elastic member between the first joint engagement section and the second joint engagement section. With this, when the first joint engagement section and the second joint engagement section rotate, the predetermined frictional force is generated between the first joint engagement section and the elastic member and between the second joint engagement section and the elastic member, which enables assured control of the movability of each arm section. Further, deterioration due to friction, etc., occurred between the first joint engagement section and the second joint engagement section can be avoided.

Further, it is preferable that the joint section is provided with an iris engagement assisting section for engaging a pupillary edge of an iris. With this, the pupil edge of the iris is engaged by the iris engagement assisting section, and therefore the pupil expander can be arranged more safely and the expanded state of the pupil can be maintained more assuredly.

Further, it is preferable that the joint section is provided with a device insertion hole for inserting a medical device for ophthalmologic surgery. With this, by inserting a medical device for ophthalmologic surgery, it becomes easy to apply a force radially inward or radially outward of the joint section. This enables easy and assured deformations of the entire shape of the pupil expander inside an eye.

Further, it is preferable that the arm sections are arranged such that the first joint engagement section provided at one end section is positioned above the second joint engagement section provided at the other end section of an adjacent arm section, and the second joint engagement section provided at the other end section is positioned below the first joint engagement section provided at one end section of an adjacent arm section, so that each arm section is arranged in an inclined state in a circumferential direction. With this, by arranging each arm section in an inclined state in the circumferential direction, a difference in height is generated in the up-down direction between both end sections in each arm. Therefore, when the pupil expander is arranged, the pupillary edges of the iris are engaged by and between both end sections of each arm section, which can expand the pupil more largely.

Further, it can be configured such that the arm sections include an upper arm section in which the first joint engagement section provided at one end section is positioned above the second joint engagement section provided at the other end section of an adjacent arm section, and the second joint engagement section provided at the other end section is positioned above the first joint engagement section provided at the other end section of an adjacent arm section, and a lower arm section in which the first joint engagement section provided at one end section is positioned below the second joint engagement section provided at the other end section of an adjacent arm section, and the second joint engagement section provided at the other end section is positioned below the first joint engagement section provided at the other end section of an adjacent arm section. The upper arm section and the lower arm section are alternately arranged along the circumferential direction.

Further, it is preferable that the arm section is curved in a manner as to expand radially outward. With this, since each arm section is arranged near the iris edge or the iris edge outside of the pupil, during surgery, the surgical field of the pupil P section can be widened, enabling more easy surgery.

EFFECTS OF THE INVENTION

According to the present invention, since the end sections of adjacent arm sections are connected in a movable manner, the entire shape of the pupil expander can be deformed in an eye via the joint section. This enables safe arrangement without damaging an iris, which in turn can maintain a sufficiently expanded state of the pupil easily and assuredly. For this reason, any operators can arrange and remove the pupil expander at ease, which in turn can reduce the effort and time for the surgery.

DETAILED DESCRIPTION OF THE PREFERRED EMBODIMENTS

<First Embodiment>

Next, a first embodiment of a pupil expander according to the present invention will be explained with reference to FIGS. 1 to 6.

[Structure of Pupil Expander]

Figure 1:
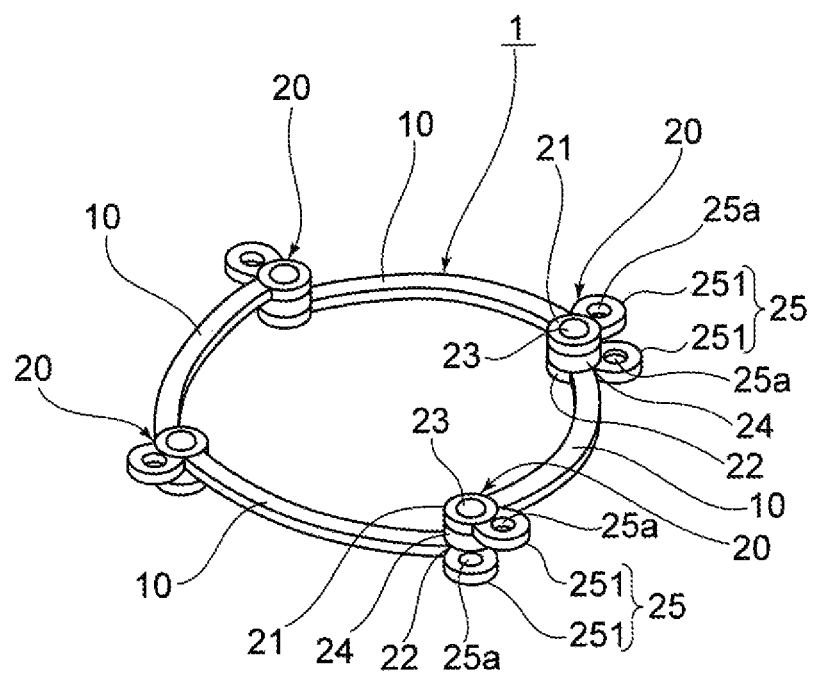
FIG. 1 is a perspective view of a pupil expander according to a first embodiment.

The pupil expander 1 according to this embodiment is used to maintain a pupil in an expanded state during ophthalmologic surgery such as cataract surgery, and, as shown in FIGS. 1 and 2, includes four arm sections 10 serially arranged in a circular manner, and joint sections 20 each connecting end sections of adjacent arm sections 10. This pupil expander 1 can be made of various materials, but is preferably made of a hard resin such as polypropylene, PMMA, hard silicon, etc., or metal such as titan, stainless steel, etc.

Figure 4A:
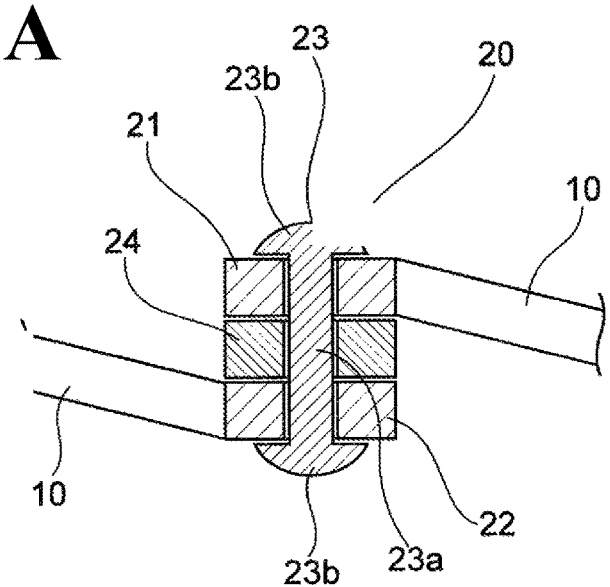
FIG. 4A is a cross-sectional view of a joint section of the pupil expander and FIG. 4B is a plan view of the arm section.
Figure 4B:
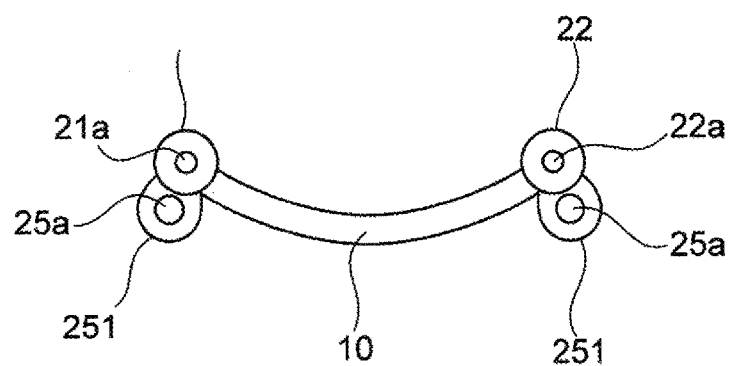

The arm sections 10 are, as shown in FIGS. 1 and 2, members each formed into the same size and the same shape and made of a rigid material, and are each, as shown in FIG. 4B, a plate-shaped elongated member extending in one direction (right-left direction in FIG. 4A). Each arm section 10 is provided with, as will be explained later, a first joint engagement section 21 of the joint section 20 on one side (left side in FIG. 4B) in the circumference direction, and a second joint engagement section 22 of the joint section 20 on the other side (right side in FIG. 4B) in the circumference direction.

Figure 2A:
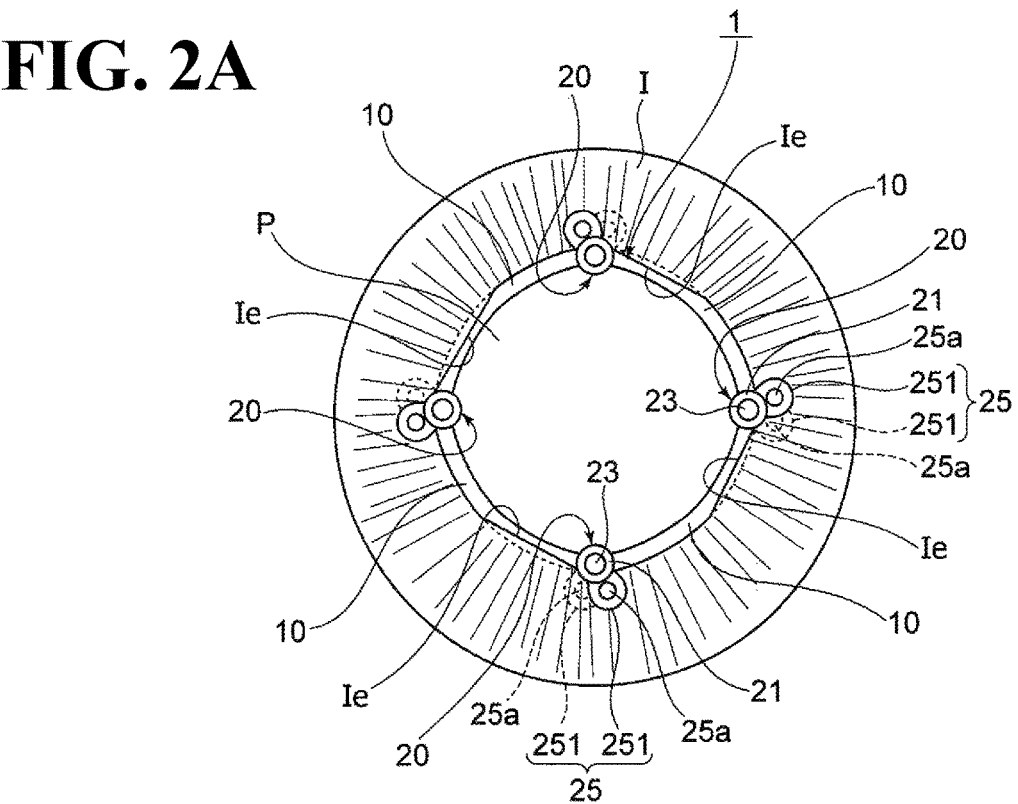
FIG. 2A is a plan view of the pupil expander in an open state and FIG. 2B is a plan view of the pupil expander in a closed state.

Further, each arm section 10 is formed into a slightly curved shape between both end sections, and as shown in FIG. 2A, in cases where arm sections are arranged serially in a manner as to form a circular shape, each arm section is curved in a manner as to expand radially outward. With this, as shown in FIG. 2A, since each arm section 10 is arranged near the iris edge 1e or outside the iris edge 1e of the pupil P, during surgery, the surgical field of the pupil P section can be widened, enabling more easy surgery.

In the arm section 10 of this embodiment, the linear length between both end sections is set to 4.5 mm, the width is set to 0.2 mm, and the thickness is set to 0.15 mm.

As shown in FIG. 1 and FIG. 2, the joint section 20 connects end sections of adjacent arm sections 10 in a movable manner. Explaining specifically, this joint section 20 includes a first joint engagement section 21 provided at one end section of one of adjacent arm sections 10 on one side, a second joint engagement section 22 provided at the other end section of one of adjacent arm sections 10 on the other side, a rotation shaft 23 rotatably sporting the first joint engagement section 21 and the second joint engagement section 22, an elastic member 24 arranged between the first joint engagement section 21 and the second joint engagement section 22, and an iris engagement assisting section 25 for retaining a pupillary edge 1e of the iris I.

Each joint section 20 rotatably moves each arm section 10 with respect to an adjacent arm section in a plain direction within a range of 0 to 180 degrees.

The first joint engagement section 21 is, as shown in FIG. 4B, formed at one end section (left end section in FIG. 4B) of the arm section 10 in the circumferential direction, and an insertion hole 21a for inserting the rotation shaft 23 is formed in the central portion of the first joint engagement section 21. On the other hand, the second joint engagement section 22 is formed at the other end section (right end section of FIG. 4B) of the arm section 10 in the circumferential direction, and an insertion hole 22a for inserting a rotation shaft 23 is formed in the central portion of the second joint engagement section 22.

Figure 3:
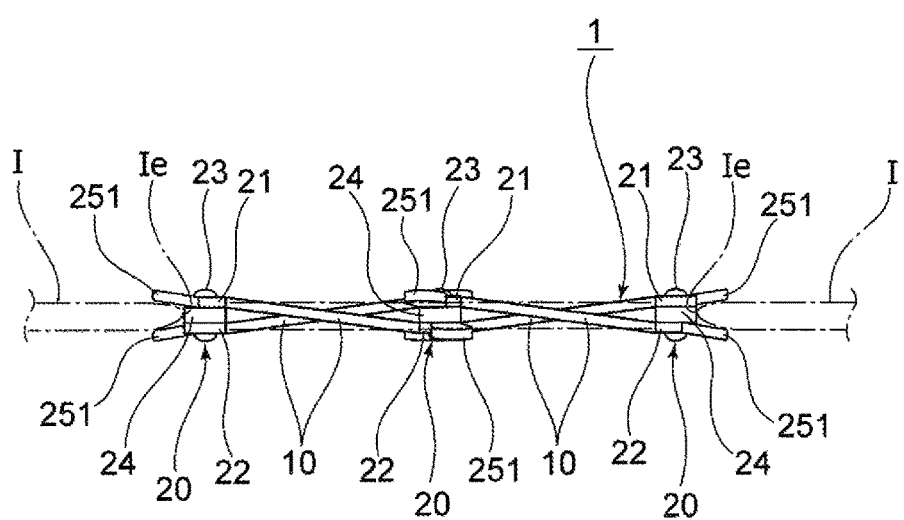
FIG. 3 is a side view of the pupil expander in an open state.

In each joint section 20, as shown in FIG. 3, the first joint engagement section 21 formed at one end section of the arm section 10 is positioned above the second joint engagement section 22 formed at the other end section of the adjacent arm section 10. Further, the second joint engagement section 22 formed at the other end section of the arm section 10 is positioned below the first joint engagement section 21 formed at one end section of the adjacent arm section 10. For this reason, as shown in FIG. 3, each arm section 10 is arranged in an inclined state in the circumferential direction.

As mentioned above, by arranging each arm section 10 in an inclined state in the circumferential direction, since a height difference occurs in the up-down direction between both end sections in each arm section 10, as shown in FIG. 2A, when the pupil expander 1 is arranged, the pupil P can be expanded more largely with the pupillary edges 1e of the iris I being engaged between end sections of arm sections 10.

In this embodiment, the first joint engagement section 21 and the second joint engagement section 22 are each formed into a disk shape having a diameter of 0.6 mm. The distance between the first joint engagement section 21 and the second joint engagement section 22 is set to 0.3 mm.

The rotation shaft 23 has, as shown in FIG. 4A, a shaft portion 23a extending in the vertical direction, and is inserted in the insertion holes 21a and 22a of the first joint engagement section 21 and the second joint engagement section 22 to rotatably support the first joint engagement section 21 and the second joint engagement section 22. With this, the first joint engagement section 21 and the second joint engagement section 22 can rotate in plain directions parallel with each other via the rotation shaft 23, and therefore each of arm sections 10 arranged adjacent via the first joint engagement section 21 and the second joint engagement section 22 becomes movable in a planner direction. As a result, the entire shape of the pupil expander 1 can be easily deformed in the planer direction.

Further, the upper end section and the lower end section of the rotation shaft 23 are each swaged into a semicircular head portion 23b. This prevents the rotation shaft 23 from being pulled out from the insertion holes 21a and 22a of the first joint engagement section 21 and the second joint engagement section 22. Further, the first joint engagement section 21 and the second joint engagement section 22 are strongly sandwiched by and between the head portions 23b of the rotation shaft 23 via the elastic member 24. This generates a predetermined frictional force between the first joint engagement section 21 and the second joint engagement section 22 as will be explained later.

The elastic member 24 is a member having a thickness of 0.3 mm and made of, silicon, polyurethane, or natural rubber, etc., and is arranged in a manner as to be in close contact with both the first joint engagement section 21 and the second joint engagement section 22 as shown in FIG. 4A. With this, when the first joint engagement section 21 and the second joint engagement section 22 rotate via the rotation shaft 23, a predetermined frictional force can be generated between the elastic member 24 and the first joint engagement section 21 and between the elastic member 24 and the second joint engagement section 22. The "predetermined frictional force" preferably has such a magnitude that, at the time of arranging or removing the pupil expander 1, the first joint engagement section 21 and the second joint engagement section 22 do not rotate by a force received from intraocular tissues such as the iris I, etc., and the first joint engagement section 21 and the second joint engagement section 22 rotate by a force from the operator via a medical device such as a Sinskey hook, etc.

As mentioned above, by generating a predetermined frictional force between the first joint engagement section 21 and the second joint engagement section 22 of the joint section 20 by the elastic member 24, the movement of each of the adjacent arm sections 10 can be controlled. Therefore, since each of the arm sections 10 can be maintained in a state in which arm sections are crossed at an arbitrary angle, even if an external force is received from intraocular tissues such as, e.g., iris I, the entire shape of the pupil expander 1 can be maintained assuredly. Further, in this embodiment, since the elastic member 24 is arranged between the first joint engagement section 21 and the second joint engagement section 22, deterioration such as, e.g., abrasion occurring between the first joint engagement section 21 and the second joint engagement section 22 can also be prevented.

The iris engagement assisting section 25 is, as shown in FIGS. 1 and 2, comprised of engaging ledges 251 and 251 which are the same in size and shape and protruded radially outward from each of the first joint engagement section 21 and the second joint engagement section 22. These engaging ledges 251 and 251 are, as shown in FIG. 3, arranged vertically in a manner as to partially overlap when the pupil expander 1 is in a circularly or approximately circularly opened state. Therefore, when the pupil expander 1 is arranged to the iris I of the pupillary edge 1e, the iris I of the pupillary edge 1e is engaged between both engaging ledges 251 and 251 of the iris engagement assisting section 25. This enables safe arrangement of the pupil expander 1 and assured maintenance of the expanded state of the pupil P. Further, in this embodiment, both the engaging ledges 251 are formed so that the tip end sections thereof depart gradually as it advances radially outward. Thus, the introduction of the pupillary edge 1e of the iris I in between both engaging ledges 251 can be performed easily.

In this embodiment, the iris engagement assisting section 25 is formed so that the engaging ledge 251 extends from each of the joint engagement sections 21 and 22 radially outward by a length of 0.6 mm.

Further, in the iris engagement assisting section 25, as shown in FIG. 4, a device insertion hole 25a is formed in both engaging ledges 251. For this reason, at the time of arranging and removing the pupil expander 1, by inserting a Sinskey hook F for example into the device insertion hole 25a, it becomes easy to apply a force radially inward or radially outward of the joint section 20. This enables easy and assured deformation of the entire shape of the pupil expander 1 within an eye.

Figure 2B:
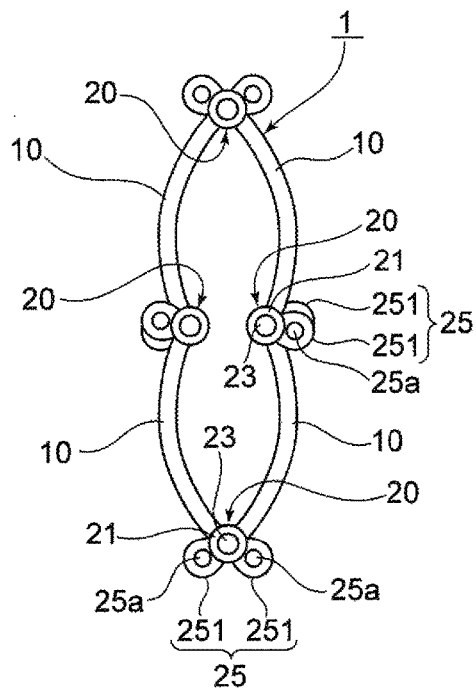

Considering the scale (length, width, thickness, intervals, etc.) of each structure of the aforementioned pupil expander 1, as shown in FIG. 2B, when the pupil expander 1 is deformed into an elongated substantially rod shape as a whole, the width of the pupil expander 1 can become about 2.2 mm. As a result, it becomes possible to insert the pupil expander into an eye through a very small incision H1 of about 2.5 to 3.0 mm. Further, the length of the pupil expander 1 becomes about 9.8 mm when the width thereof is about 2.2 mm, and therefore when inserting the entire pupil expander 1 into an eye, the risk of damaging the endothelium or the angle of the cornea Co is very low since the inner side long diameter of the cornea Co (the distance from one angle to the other angle) in the eye (in the anterior chamber) is 12 mm. Therefore, when the pupil expander 1 is arranged at the pupillary edge 1e of the iris I, it is possible to expand the pupil P so that the maximum diameter becomes 6 mm and the minimum diameter becomes 5.2 mm.

[Method of Arranging and Removing Pupil Expander]

Next, the arranging and removing the pupil expander 1 will be explained with reference to FIGS. 5 and 6. Hereinafter, in the cornea Co, preliminarily, an incision H1 for inserting the pupil expander 1 is formed in a manner such that the diameter thereof is about 2.5 to 3.0 mm, and at both right and left sides of the incision H1 in the cornea Co, side ports (incisions) H2 or H3 for inserting a Sinskey hook F is formed in a manner such that the diameter is about 1.0 mm. These incision H1 and side ports (incisions) H2 and H3 are shown by broken lines in figures.

Figure 5A:
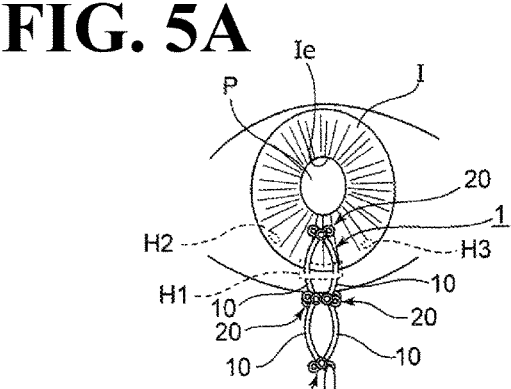
FIGS. 5A to 5D are plan views showing an arrangement of the pupil expander shown in FIG. 1 in a stepwise manner.
Figure 5E:
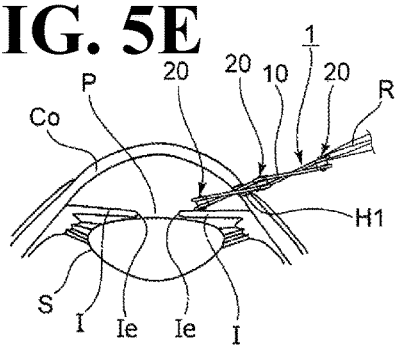
FIGS. 5E to 5H are side views of the arrangement thereof.

Initially, when arranging the pupil expander 1, as shown in FIGS. 5A and 5E, a viscoelastic material is injected into the anterior chamber in a manner as to attain the state in which the space between the cornea Co and the iris I is kept deep, and each of the arm sections 10 is moved via the joint section 20 (rotation shaft 23) to thereby deform the pupil expander 1 into a closed state (in an entirely elongated approximately bar-shaped state). While pinching one end section (lower end in FIG. 5A) of this pupil expander 1 by a forceps R, the pupil expander 1 is inserted into an eye through the incision H1 so that the pupil expander 1 is arranged above the iris I. As explained above, when the pupil expander 1 is in an elongated approximately bar-shape as a whole, the pupil expander 1 is arranged so that the pair of joint sections 20 (concretely, the pair of ledges 251 of the iris engagement assisting section 25) in a proximately positioned state are positioned inside the pupillary edge 1e of the iris I.

It is configured such that the pupil expander 1 is naturally arranged at the aforementioned position when the pupil expander is positioned at the center of anterior chamber. Further, when the arrangement position of the pupil expander 1 is inappropriate, the position of the pupil expander 1 may be corrected with two Sinskey hooks F inserted through the side ports H2 and H3. Further, at this stage, in a state in which the lower end section of the pupil expander 1 pinched by the forceps R is protruded from the incision H1, the next operation can be performed. Further, the insertion of the pupil expander 1 into an eye can be performed using an injector.

Figure 5B:
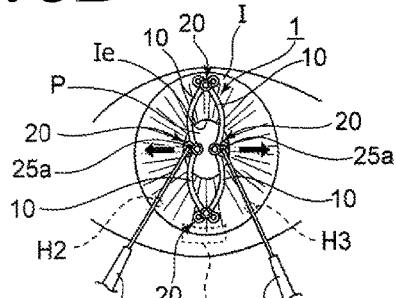
Figure 5F:
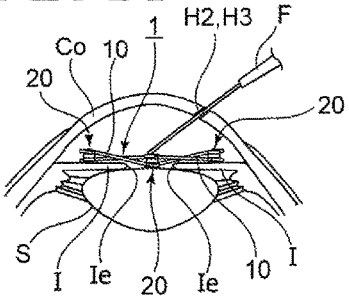

Next, as shown in FIGS. 5B and 5F, each of the tip end portions of the two Sinskey hooks F inserted through the side ports H2 and H3 is inserted into each of the device insertion holes 25a positioned outside the pair of joint sections 20 in a closely positioned state, and the pupillary edge 1e of the iris I is opened in a direction in which the pupillary edges separate from each other (the right-left direction in FIG. 5B) in a state in which the pupillary edge 1e of the iris I is engaged with the outer side portion of the joint section 20. At this time, the pair of joint sections 20 which are in a closely approached state (joint sections positioned in the right-left direction in FIG. 5B) move both the arm sections 10 so as to decrease the angle between the arm sections 10 positioned on both sides. While, the pair of joint sections 20 which are in a separated state (joint sections positioned in the up-down direction in FIG. 5B) move both the arm sections 10 so as to increase the angle between the arm sections 10 positioned on both sides. When opening the joint sections 20 in the right-left direction, they are opened until the pair of joint sections which were in a separated state (joint sections positioned in the up-down direction in FIG. 5B) becomes in a closely approached state.

Further, when opening the joint sections 20 while engaging the pupillary edge 1e of the iris I between both engaging ledges 251 of the iris engagement assisting section 25 provided at the joint section 20, by positioning the pair of joint sections 20 lateral to the pupillary edge 1e of the iris I at the previous step, for a cataract patient having an experience of using a Sinskey hook F, etc., the operation can be performed easily. Further, since both the upper and lower engaging ledges 251 are 0.6 mm in length and the same in shape, a compressing force and an expanding force can be applied to the iris I symmetrically in the right-left and front-back directions at a wide area, resulting in less invasion to the iris I.

Figure 5C:
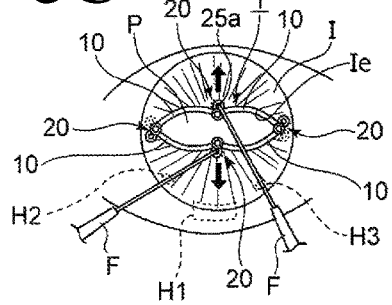
Figure 5G:
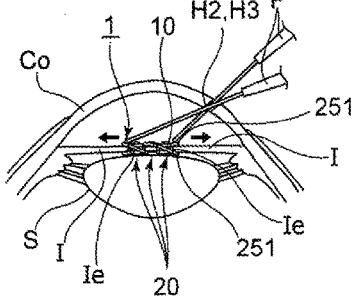

Next, as shown in FIGS. 5C and 5G, each of tip end sections of Sinskey hooks F is inserted into each device insertion hole 25a located outside the pair of joint sections 20 in an approached state caused by the last operation (joint sections positioned in the up-down direction in FIG. 5C), the pupillary edges 1e of the iris I are opened in a direction separating each other while being engaged with the outside sections of the joint sections. At this time, the pair of joint sections 20 which are in a closely approached state (joint sections positioned in the up-down direction in FIG. 5C) move both the arm sections 10 so as to decrease the angle between the arm sections 10 positioned on both sides. While, the pair of joint sections 20 which are in a separated state (joint sections positioned in the right-left direction in FIG. 5C) move both the arm sections 10 so as to increase the angle between the arm sections 10 positioned on both sides. When opening the joint sections 20 in the up-down direction, the joint sections 20 are opened until the angles between the joint sections 20 become even.

Figure 5D:
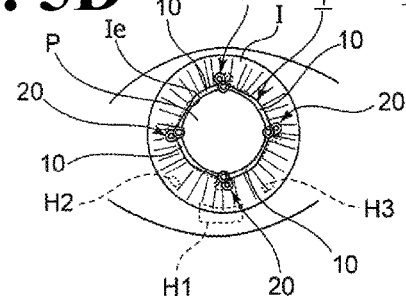
Figure 5H:
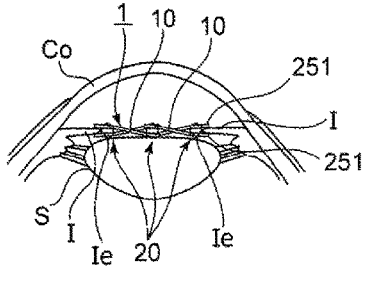

As a result, as shown in FIGS. 5D and 5H, each joint section 20 engages the pupillary edge 1e of the iris I. Further, since each arm section 10 is in an inclined state, the pupillary edge 1e of the iris I is engaged between both end sections of the arm sections 10. For this reason, the pupil expander can be safely arranged without damaging the iris I, which enables easy and assured maintenance of the sufficiently expanded state of the pupil.

Figure 6A:
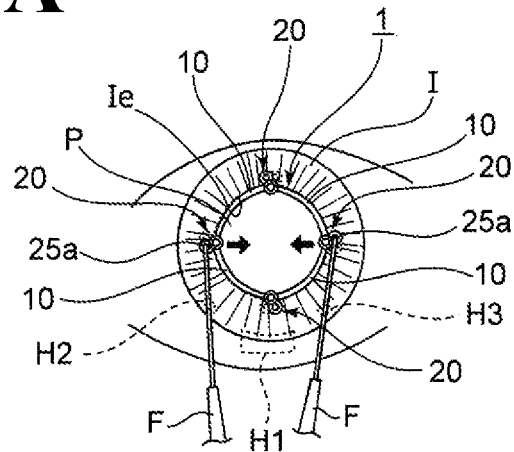
FIGS. 6A to 6C are plan views showing a removal of the pupil expander shown in FIG. 1 in a stepwise manner.

On the other hand, as for the removal of the pupil expander 1 after completion of intraocular surgery such as, e.g., cataract surgery, as shown in FIG. 6A, after securing a space in the anterior chamber by injecting viscoelastic material, the tip end sections of two Sinskey hooks F inserted through the side ports H2 and H3 are inserted into the respective device insertion holes 25a of the pair of joint sections 20 (positioned in the right-left direction in FIG. 6A). Then, the pair of joint sections 20 are closed in the approaching direction to thereby deform the entire shape of the pupil expander 1 into an elongated substantially rod shape in the eye via the joint sections 20.

Figure 6B:
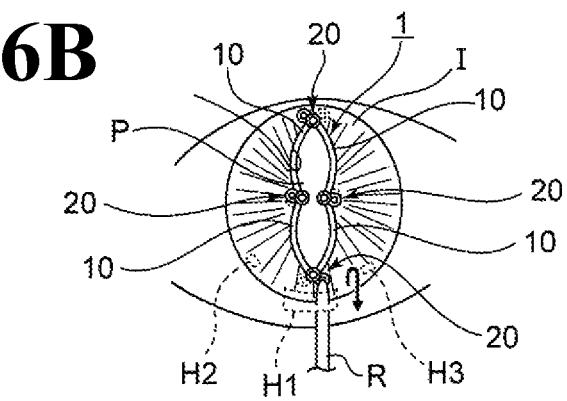

Next, as shown in FIG. 6B, the one end section of the pupil expander 1 (the lower end section in the figure), which is in an elongated substantially rod shape as a whole, is pinched by forceps R, and as shown in the arrow in the figure, while slightly pushing toward the back side (upward in FIG. 6B) and pulling up, the engaging ledges 251 of the iris engagement assisting section 25 of the one end section of the pupil expander 1 are detached from the pupillary edge 1e of the iris I.

Figure 6C:
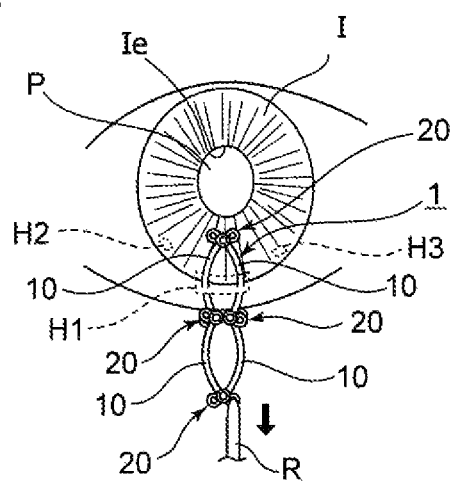

Next, as shown in FIG. 6C, by pulling toward the front side (downward in FIG. 6C) from the state to exenterate through the incision H1 to an outside of the eye. Thus, the pupil expander 1 can be removed.

In this embodiment, the explanation was directed to the case in which the pupil expander 1 is deformed into an elongated substantially rod shape as a whole at the time of arranging the pupil expander 1. However, the pupil expander can be in a previously deformed state. For example, at the time of shipping the pupil expander 1, the pupil expander 1 can be deformed in an elongated substantially rod shape.

Figure 7:
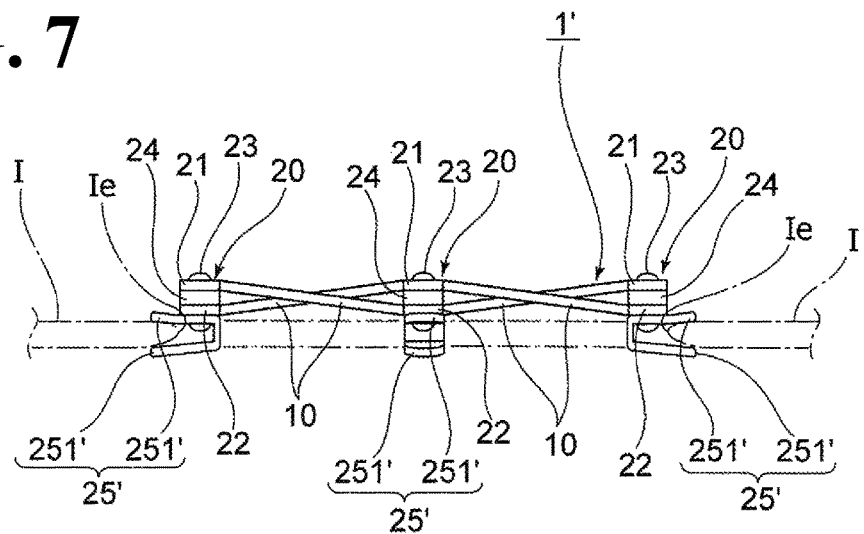
FIG. 7 is a side view showing another modified embodiment of an iris engagement assisting section.

Further, the above explanation was directed to the case in which the iris engagement assisting section 25 includes engaging ledges 251 each radially outwardly protruded from the first joint engagement section 21 or the second joint engagement section 22, but the iris engagement assisting section 25 can be formed into another shape. For example, as shown in FIG. 7, the iris engagement assisting section 25' of the pupil expander 1' can be formed into a U-shape as seen from the side and formed below the joint section 20.

Further, the explanation was directed to the case in which the rotation shaft 23 is provided with head portions 23b at the upper and lower end sections, but the head portion 23b is not always required to be provided.

Further, the case in which the head portions 23b of the rotation shaft 23 are formed by swaging was explained, but it can be configured such that head portions 23b are detachably attached to the upper and lower sections of the shaft portion 23a of the rotation shaft 23.

Figure 8:
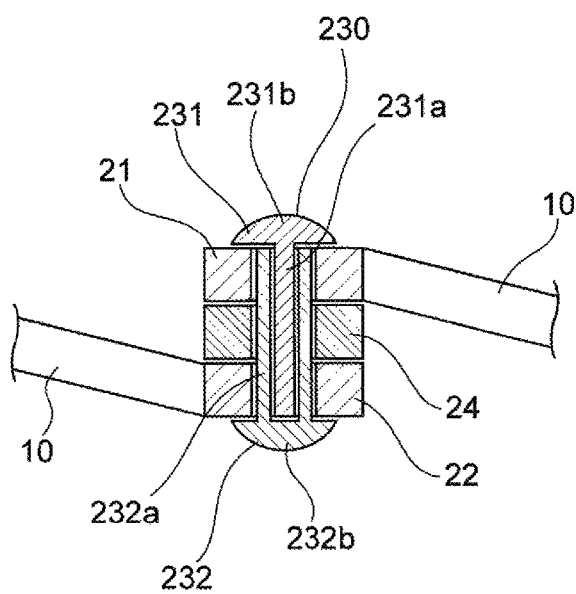
FIG. 8 is a cross-section showing another modification of a rotation shaft.

Further, it was explained that the shaft portion 23a of the rotation shaft 23 is formed by a single bar-shaped member, but the shaft portion can be any other structure. For example, the rotation shaft 230 shown in FIG. 8 is provided with an upper shaft member 231 having a head portion 231b at an upper end section and a shaft portion 231a extending downward, and a lower shaft member 232 having a head portion 232b at a lower end section and a cylindrical portion 232a extending upward. The shaft portion 231a of the upper shaft member 231 is inserted into the insertion hole 21a of the first joint engagement section 21, and the cylindrical portion 232a of the lower shaft member 232 is inserted into the insertion hole 22a of the second joint engagement section 22. Then, the upper shaft member 231 is fitted in the lower shaft member 232 and fixed thereto.

<Second Embodiment>

Next, a second embodiment of a pupil expander according to the present invention will be explained with reference to FIGS. 9 and 10. Hereinafter, the explanation will be directed only to the structure different from the aforementioned embodiment, and explanations will be omitted for the same structure by allotting the same symbol.

Figure 9:
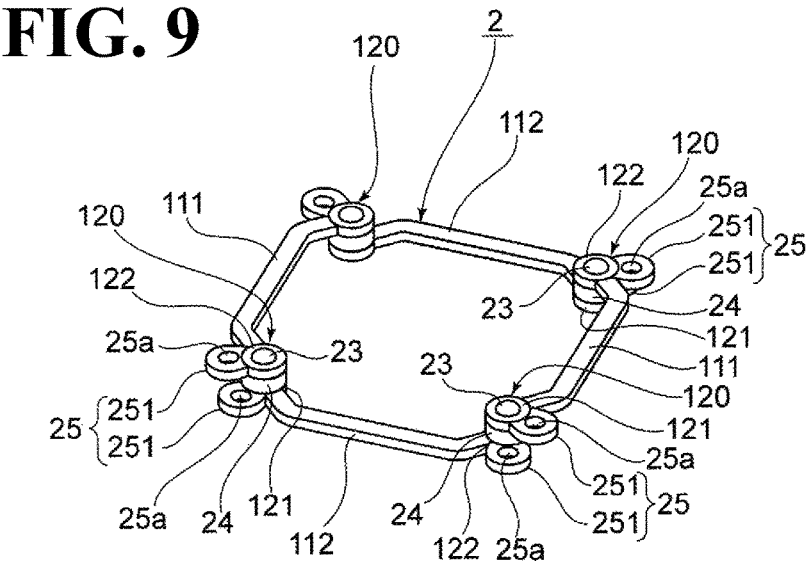
FIG. 9 is a perspective view of a pupil expander according to a second embodiment.
Figure 10:
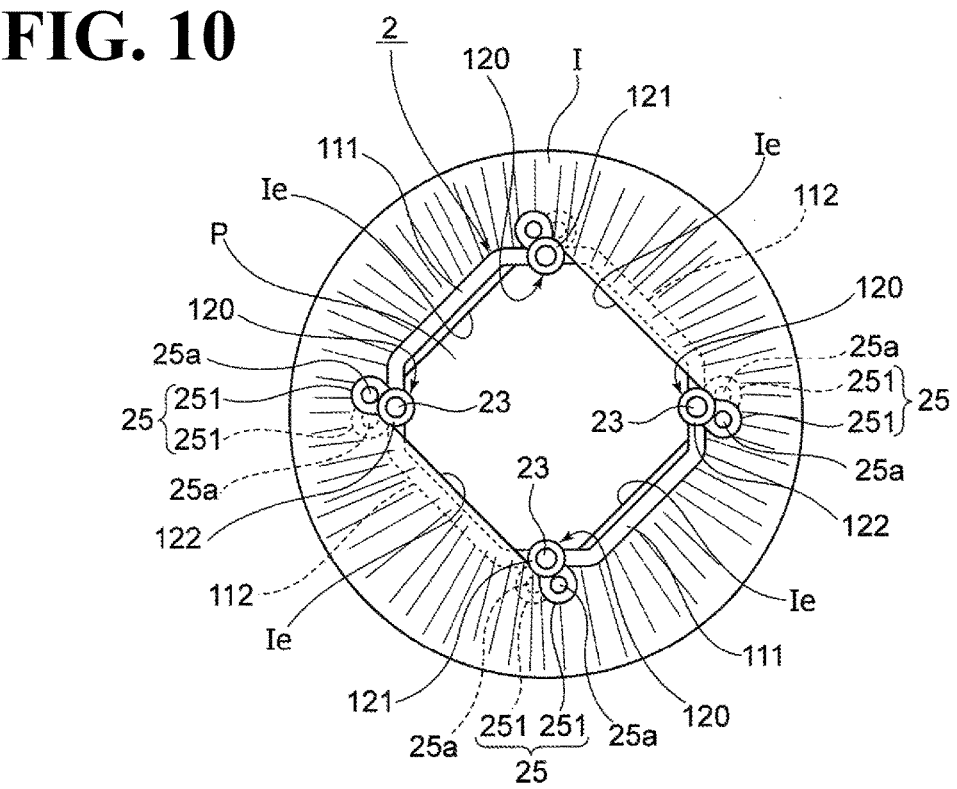
FIG. 10 is a plan view of the pupil expander in an open state.

The pupil expander 2 of this embodiment is, as shown in FIGS. 9 and 10, provided with two upper arm sections 111 and two lower arm sections 112 arranged in a manner as to form a circular shape, and joint sections 120 connecting end sections of adjacent arm sections 111, 111, 112 and 112.

The arm sections 111, 111, 112 and 112 are, as shown in FIGS. 9 and 10, members each made of a rigid material and formed into the same size and shape, and each provided with a first joint engagement section 121 of the joint section 120 on one side in the circumferential direction and a second joint engagement section 122 of the joint section 120 on the other side in the circumferential direction.

In the upper arm section 111, the first joint engagement section 121 provided at one end section is positioned above the second joint engagement section 122 provided at the other end section of the adjacent lower arm section 112, and the second joint engagement section 122 provided at the other end section is positioned above the first joint engagement section 121 provided at one end section of the adjacent lower arm section 112. On the other hand, in the lower arm section 112, the first joint engagement section 121 provided at one end section is positioned below the second joint engagement section 122 provided at the other end section of the adjacent lower arm section 111, and the second joint engagement section 122 provided at the other end section is positioned below the first joint engagement section 121 provided at the other end section of the adjacent upper arm section 111.

Further, between the first joint engagement section 121 or the second joint engagement section 122 of the upper arm section 111 and the second joint engagement section 122 or the first joint engagement section 121 of the lower arm section 112, an elastic member 24 is arranged. This elastic member 24 is a member having a thickness of 0.3 mm and made of a material such as silicon, polyurethane, natural rubber, etc., and is arranged in a manner as to be in close contact with both the first joint engagement section 121 and the second joint engagement section 122. With this, when the first joint engagement section 121 and the second joint engagement section 122 rotate via the rotation shaft 23, a predetermined frictional force can be generated between the elastic member 24 and the first joint engagement section 121 and between the elastic member 24 and the second joint engagement section 122.

<Third Embodiment>

Next, a third embodiment of a pupil expander according to the present invention will be explained with reference to FIG. 11 Hereinafter, only the structures different from those of the aforementioned embodiments will be explained, and explanations of the same structures as those of the aforementioned embodiments will be omitted by allotting the same symbols.

Figure 11:
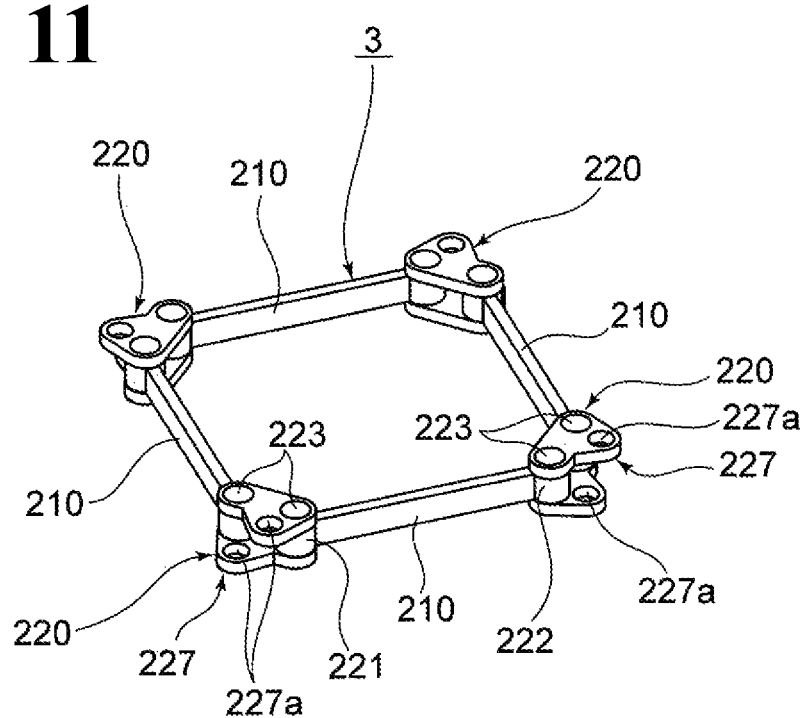
FIG. 11 is a perspective view of a pupil expander according to a third embodiment.

The pupil expander 3 of this embodiment is, as shown in FIG. 11, provided with four arm sections 210 arranged in a manner as to form a circular shape and joint sections 220 connecting the end sections of adjacent arm sections 210.

As shown in FIG. 11, the arm sections 210 are members each made of a rigid member formed into the same shape, and are each provided with a first joint engagement section 221 of a joint section 220 on one side in a circumferential direction and a second joint engagement section 222 of a joint section 220 on the other side in the circumferential direction.

As shown in FIG. 11, the joint section 220 includes a first joint engagement section 221 provided at one end section of the arm section 210 in the circumferential direction, a second joint engagement section 222 provided at the other end section of the arm section 210 on the other side in the circumferential direction, and a support section 227 which supports the first joint engagement section 221 and the second joint engagement section 222 via a rotation shaft 223. This support section 227 supports the first joint engagement section 221 and the second joint engagement section 222 in a manner as to face them in the circumferential direction. The support section 227 is provided with a device insertion hole 227a.

With this, the first joint engagement section 221 and the second joint engagement section 222 rotate in plain surfaces parallel with each other via a support section 227, and therefore the entire shape of the pupil expander 3 can be deformed in the plane direction.

In each embodiment, the arm section is formed in a manner as to curve radially outward. However, the arm section is not required to be curved.

The above explanations were directed to the case in which there are four arm sections. However, the number of arm sections may be five or more.

In each arm section, the rotational movement is controlled by a predetermined force by an elastic member. However, the rotational movement of each arm section may be controlled by another method.

Further, the joint section is configured to move the arm section via the rotation shaft, but the arm section can be moved by a mechanism other than the rotation shaft.

Although the explanation was directed to the case in which the joint section is provided with a first joint engagement section and a second joint engagement section, and the first joint engagement section and the second joint engagement section are movable, the end sections of adjacent arm sections can be joined movably by another structure.

The above explanation was directed to the case in which the rotation shaft 23 is provided with the head portion 23b. However, it is not always required to have such a head portion.

The above explanation was directed to the case in which the device insertion hole 25a is provided. However, it is not always required to have such a device insertion hole.

The above explanation was directed to the case in which the iris engagement assisting section 25 is provided. However, it is not always required to have such an iris engagement assisting section.

It should be noted that the scale (length, width, thickness, intervals, ect.) of each structure is exemplarily shown as an example, and not limited to it.

Although embodiments of the present invention was explained with reference to the drawings, the present invention is not limited to the illustrated embodiments. Various modifications and/or deformations can be added to the illustrated embodiments within the same scope or within the equivalent range of the present invention.

The invention claimed is:

1. A pupil expander to be used to maintain an expanded state of a pupil during ophthalmologic surgery, comprising:
    four or more arm sections serially arranged in a manner as to form a circular shape when in the expanded state; and
    a plurality of joint sections,
    wherein each joint section includes
        a first joint engagement section provided at a first end section of an arm section on one side in a circumferential direction,
        a second joint engagement section provided at a second end section of an adjacent arm section in the circumferential direction, and
        a rotational control member positioned between the first joint engagement section and the second joint engagement section, wherein the rotational control member includes an elastic member between the first joint engagement section and the second joint engagement section, the elastic member contacting respective surfaces of each of the first joint engagement section and the second joint engagement section to generate a predetermined frictional force for controlling rotational movements of the first joint engagement section and the second joint engagement section, and
    wherein each joint section is configured to connect the first end section of an arm section and the second end section of an adjacent arm section.

2. The pupil expander as recited in claim 1, wherein the first joint engagement section and the second joint engagement section are rotatable with respect to each other.

3. The pupil expander as recited in claim 2, wherein at least two arm sections of the four or more arm sections are arranged such that the first joint engagement section provided at the end section is positioned above the second joint engagement section provided at the end section of the adjacent arm section, and the second joint engagement section provided at the end section of the adjacent arm section is positioned below the first engagement section.

4. The pupil expander as recited in claim 2, wherein each arm section of the four or more arm sections includes:
    an upper arm section in which the first joint engagement section provided at one end section is positioned above the second joint engagement section provided at the other end section of an adjacent arm section, and the second joint engagement section provided at the other end section is positioned above the first joint engagement section provided at the other end section of an adjacent arm section; and
    a lower arm section in which the first joint engagement section provided at one end section is positioned below the second joint engagement section provided at the other end section of an adjacent arm section, and the second joint engagement section provided at the other end section is positioned below the first joint engagement section provided at the other end section of an adjacent arm section,
    wherein the upper arm section and the lower arm section are alternately arranged along the circumferential direction.

5. The pupil expander as recited in claim 2, wherein, for each joint section, the first joint engagement section and the second joint engagement section are rotatable about a common rotation shaft.

6. The pupil expander as recited in claim 2, wherein the joint section is provided with a support section which rotatably supports the first joint engagement section and the second joint engagement section in a manner as to configure the first joint engagement section and the second joint engagement section to face each other in a circumferential direction.

7. The pupil expander as recited in claim 1, wherein the joint section is provided with an iris engagement assisting section for engaging a pupillary edge of an iris.

8. The pupil expander as recited in claim 1, wherein the joint section is provided with a device insertion hole for inserting a medical device for ophthalmologic surgery.

9. The pupil expander as recited in claim 1, wherein at least one arm section of the four or more arm sections is configured to expand outwardly in a radial direction.

10. A pupil expander used to maintain an expanded state of a pupil during ophthalmologic surgery comprising:
    at least four arm sections serially arranged in a manner as to form a circular shape in the expanded state; and
    a plurality of joint sections, wherein each joint section includes
    a first joint engagement section provided on a first end of a first arm section,
    a second joint engagement section provided on a second end of a second arm section,
    a rotational control member, wherein the rotational control member includes an elastic member between the first joint engagement section and the second joint engagement section, the elastic member contacting respective surfaces of each of the first joint engagement section and the second joint engagement section to generate a predetermined frictional force for controlling movements of the first joint engagement section and the second joint engagement section, and
    a rotation shaft to rotatably support the first joint engagement section, the second joint engagement section, and the rotational control member.

* * * * *